United States Patent
Soundara Pandian et al.

(10) Patent No.: US 10,322,929 B2
(45) Date of Patent: Jun. 18, 2019

(54) MONOLITHIC INTEGRATION OF PMUT ON CMOS

(71) Applicant: Silterra Malaysia Sdn. Bhd., Kulim (MY)

(72) Inventors: Mohanraj Soundara Pandian, Kulim (MY); Arjun Kumar Kantimahanti, Kulim (MY)

(73) Assignee: Silterra Malaysia Sdn. Bhd., Kulim (MY)

( * ) Notice: Subject to any disclaimer, the term of this patent is extended or adjusted under 35 U.S.C. 154(b) by 0 days.

(21) Appl. No.: 15/875,208

(22) Filed: Jan. 19, 2018

(65) Prior Publication Data

US 2019/0100427 A1   Apr. 4, 2019

(30) Foreign Application Priority Data

Sep. 29, 2017 (MY) .............................. PI2017703695

(51) Int. Cl.
 *B81B 7/00* (2006.01)
 *B06B 1/06* (2006.01)
 *G01N 29/24* (2006.01)

(52) U.S. Cl.
 CPC ............ *B81B 7/008* (2013.01); *B06B 1/0644* (2013.01); *G01N 29/2437* (2013.01); *B81B 2201/0271* (2013.01); *B81B 2207/015* (2013.01)

(58) Field of Classification Search
 CPC ............ H01L 23/49827; H01L 23/522; H01L 23/5221; H01L 23/5226; H01L 23/538; H01L 23/5381; H01L 23/5384; H01L 23/5389; H01L 24/18; H01L 2224/97; H01L 41/0805; H01L 41/081; H01L 41/113; B81B 7/008; B81B 2201/0271;
 (Continued)

(56) References Cited

U.S. PATENT DOCUMENTS

2016/0009544 A1   1/2016 Rothberg et al.
2016/0009549 A1*  1/2016 Rothberg ............ B81C 1/00238
                                                       438/51
(Continued)

FOREIGN PATENT DOCUMENTS

WO         2016040333          3/2016

*Primary Examiner* — Thanh Y. Tran
(74) *Attorney, Agent, or Firm* — Preston Smirman; Smirman IP Law, PLLC

(57) ABSTRACT

This disclosure describes a monolithic integrated device that comprises a substrate layer being the base of the device, an inter-layer dielectric disposed on top of the substrate layer and below a passivation layer, an electronic circuitry formed within the inter-layer dielectric and supported by the substrate layer, the electronic circuitry comprises a plurality of metal layers formed by one or more spaced apart metals; and at least one micromachined ultrasonic transducer. Each micromachined ultrasonic transducer comprises a bottom electrode disposed on top of the passivation layer and connected to the electronic circuitry, a piezoelectric disposed on top of the bottom electrode, a top electrode disposed on top of the piezoelectric, and an elastic layer positioned on top of the top electrode. There is a cavity formed below the bottom electrode that extends from the passivation layer to a portion of the inter-layer dielectric.

15 Claims, 3 Drawing Sheets

(58) Field of Classification Search
CPC ............ B81B 2207/015; B81B 3/0021; G01N 29/2437; B06B 1/0644; B06B 1/0662
See application file for complete search history.

(56) References Cited

U.S. PATENT DOCUMENTS

2017/0252777 A1* 9/2017 Kidwell, Jr. ......... A61B 8/4483
2018/0151622 A1* 5/2018 Soundara Pandian ... H03H 9/25

* cited by examiner

MONOLITHIC INTEGRATION OF PMUT ON CMOS

CROSS-REFERENCE TO RELATED APPLICATION

The instant application claims priority to Malaysia Patent Application Ser. No. PI2017703695 filed Sep. 29, 2017, the entire specification of which is expressly incorporated herein by reference.

FIELD OF THE INVENTION

This invention relates to a monolithic integrated device. In particular, the device is a monolithic integration of piezoelectric micromachined ultrasonic transducers, PMUT with a complementary metal-oxide-semiconductor, CMOS.

BACKGROUND OF THE INVENTION

Micromachined ultrasonic transducer is an electronic device that comprises vibrating membranes capable of generating high pressure waves with an applied AC voltage signal. The generated waves travel through a medium and reflect back to the transducer when the waves meet an object. The transmitted and returned waves are electronically processed to detect information about the object including its distance, shape and other physical properties. The vibration of the membrane is enabled by either capacitive or piezoelectric transduction. Capacitive micromachined ultrasonic transducers are known as CMUT, whereas piezoelectric micromachined ultrasonic transducers are known as PMUT.

Wafer bonding is a conventional method for integrating micromachined ultrasonic transducers with complementary metal oxide semiconductor, CMOS substrates. US20160009544A1 discloses a method of integrating micromachined ultrasonic transducers with complementary metal oxide semiconductor, CMOS substrates. The micromachined ultrasonic transducers can be CMUT or PMUT. This method involves the wafer bonding technique to bind the PMUT to the substrate, as well as to connect one substrate to another. WO2016040333 describes a microelectromechanical system, MEMS device having a PMUT which is formed by an ultrasound transducer, MUT structure and a piezoelectric material. A first metal conductive layer is disposed on the piezoelectric material and a plurality of metal electrodes is configured to form electrical connections between the first metal conductive layer, the piezoelectric material, and a CMOS structure. The PMUT structure and the CMOS structure are vertically stacked, whereby the MUT structure is bonded to the CMOS structure at the standoff via wafer bonding techniques such as eutectic bonding and compression bonding.

This disclosure focuses on the micromachined ultrasonic transducer that utilizes the piezoelectrically actuated membrane. PMUT operates based on the flexural motion of a thin membrane that is coupled with a thin piezoelectric film. Various advantages offered by PMUT include increase bandwidth, provide flexible geometries, minimize voltage requirements, enable mixing of different resonant frequencies and support miniaturization of high frequency electronic devices. Typical PMUT cells are fabricated on a separate substrate and wire bond to the CMOS substrate or bond to the CMOS substrate using wafer bonding techniques. However, these bonding methods cause low fill-factor and high amount of electrical parasitic.

To enhance mechanical integrity of two connected PMUT chips, a bonding ring which is typically 10-15 um is applied around the effective PMUT area, in between the CMOS substrate and the piezoelectric. In addition, to increase electrical integrity, an additional metal line with a width of approximately 5 um is applied for connecting the piezoelectric of two adjacently positioned PMUT chips. When multiple PMUT cells are populated within a specific area, the bond ring and electrical ring occupy significant area and thus causes low fill-factor of the integrated PMUT-CMOS device.

The invention disclosed herein shall provide a solution to the abovementioned limitations and drawbacks of current integrated or connected PMUT-CMOS devices. By this invention, the PMUT cells can be placed closely to each other and improvement of the fill-factor can be achieved.

SUMMARY OF THE INVENTION

The present invention relates to a monolithic integrated device which comprises a substrate layer being the base of the device; an inter-layer dielectric disposed on top of the substrate layer and below a passivation layer; an electronic circuitry formed within the inter-layer dielectric and supported by the substrate layer, the electronic circuitry comprises a plurality of metal layers formed by one or more spaced apart metals; and at least one micromachined ultrasonic transducer, each comprising a bottom electrode disposed on top of the passivation layer and connected to the electronic circuitry; a piezoelectric disposed on top of the bottom electrode; and an elastic layer positioned on top of the piezoelectric; wherein the monolithic integrated device is formed with a cavity below each micromachined ultrasonic transducer that extends from the passivation layer to a portion of the inter-layer dielectric.

The bottom electrode is preferred to be split into two halves, whereby the first halve performs function as a bottom electrode and the second halve performs function as a top electrode.

In a preferred embodiment, the monolithic integrated device further comprises a top electrode in between the elastic layer and the piezoelectric.

The monolithic integrated device is preferred to comprise an electrical connect disposed below one or both ends of the elastic layer and connected to the electronic circuitry.

In addition, the electrical connect can have a base portion for connecting to the bottom electrode of an adjacent micromachined ultrasonic transducer.

Preferably, the electronic circuitry includes at least a source and drain component in the substrate layer.

It is also preferred that the electronic circuitry includes at least a gate in the inter-layer dielectric each connected to the source and drain component.

Further, the electronic circuitry may include at least a contact component for connecting any one or combination of the source and drain component and the gate to one of the metals.

Preferably, the monolithic integrated device further comprises one or more vias for connecting different metal layers.

In addition, it is preferred that the monolithic integrated device comprises a via contact for contacting the bottom electrode with the electronic circuitry.

In one of the preferred embodiments, the monolithic integrated device is formed with at least a bond-pad opening that extends through the passivation layer and partially into the inter-layer until the bond-pad opening reaches one of the metals.

It is preferred that the electronic circuitry is a CMOS device.

Preferred material of the elastic layer includes any one of amorphous silicon, silicon dioxide, silicon nitride, silicon carbide, metallic nitride, bimetallic nitride, or metallic oxide.

The piezoelectric can be any one of aluminium nitride, aluminium scandium nitride, lead zirconate titanate or zinc oxide.

Further another preferred embodiment of the invention is a monolithic integrated device that comprises a substrate layer being the base of the device; an inter-layer dielectric disposed on top of the substrate layer and below a passivation layer; an electronic circuitry formed within the inter-layer dielectric and supported by the substrate layer, the electronic circuitry comprises a plurality of metal layers formed by one or more spaced apart metals; and at least one micromachined ultrasonic transducer, each comprising a bottom electrode disposed on top of the passivation layer and connected to the electronic circuitry; a piezoelectric disposed on top of the bottom electrode; a top electrode disposed on top of the piezoelectric; and an elastic layer positioned on top of the top electrode; wherein the monolithic integrated device is formed with a cavity below the bottom electrode that extends from the passivation layer to a portion of the inter-layer dielectric.

In this invention, PMUT cells are integrated with the CMOS substrate to form a single unit. Such fabrication technique replaces wire bonding and wafer bonding techniques. In addition, components like bonding ring that occupies a significant space can be eliminated since a separate bonding area is no longer required. The electrical connect that allows adjacent PMUT cells to be electrically connected to each other has a miniature dimension such that it can be positioned within the effective PMUT area. The structure and configuration of PMUT cells on the CMOS substrate increase fill factor and reduce distances between neighboring PMUT cells and lowers the electrical parasitic paths. Further, a single CMOS substrate is only required for accommodating multiple PMUT cells.

DETAILED DESCRIPTION OF THE INVENTION

For a better understanding of the invention, preferred embodiments of the invention that are illustrated in the accompanying drawings will be described in detail.

A monolithic integrated device that integrates a piezoelectric micromachined ultrasonic transducers, PMUT with a complementary metal-oxide-semiconductor, CMOS is introduced in this disclosure. This invention is used in applications for detecting distances, shape or other physical properties of an object through generated waves. The applications include but not limited to medical imaging, fingerprint sensor, industry automation like collision avoidance & non-destructive testing.

Figure 1:
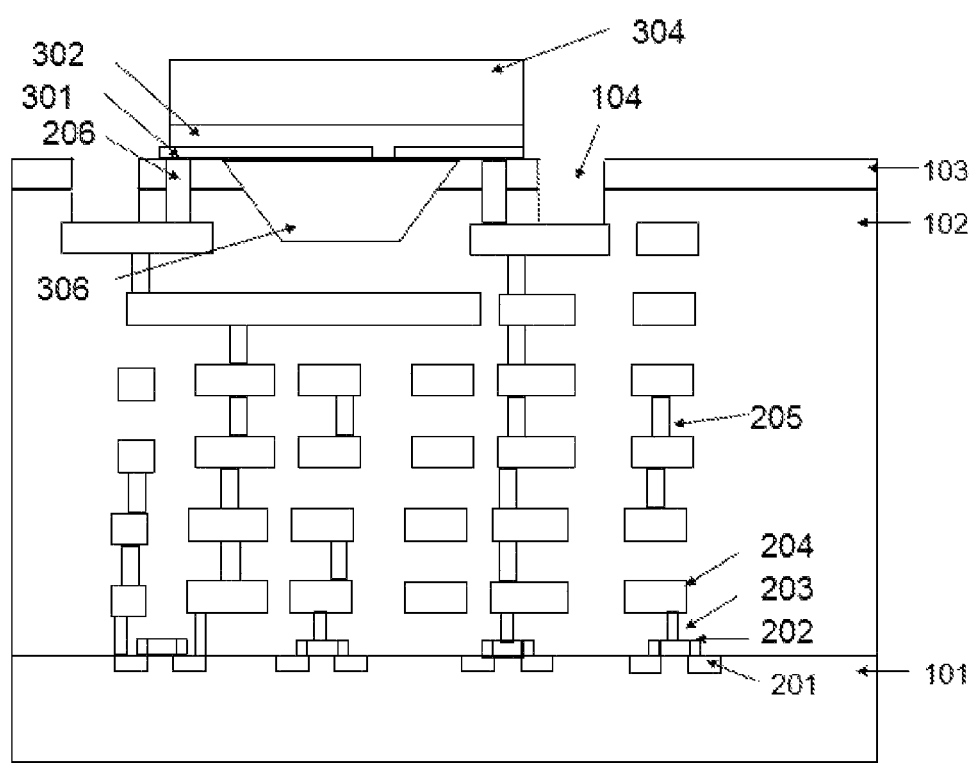
FIG. 1 shows a first preferred embodiment of a monolithic integrated device having a PMUT cell without a top electrode.

Referring to FIG. 1 that illustrates the first preferred embodiment of the invention, the monolithic integrated device comprises a substrate layer (101) being the base of the device; an inter-layer dielectric (102) disposed on top of the substrate layer (101) and below a passivation layer (103); an electronic circuitry formed within the inter-layer dielectric (102) and supported by the substrate layer (101); and at least one micromachined ultrasonic transducer. The term "electronic circuitry" used herein refers to an active circuitry that comprises an electronic component or a plurality of electronic components which are connected by electrical connections such as a CMOS device. The term "CMOS substrate" used herein refers to the electronic circuitry, substrate layer (101), inter-layer dielectric (102) and passivation layer (103), whereas "micromachined ultrasonic transducer" refers to a PMUT cell.

Each micromachined ultrasonic transducer comprises a bottom electrode (301) disposed on top of the passivation layer (103) and connected to the electronic circuitry; a piezoelectric (302) disposed on top of the bottom electrode (301); and an elastic layer (304) positioned on top of the piezoelectric (302). The bottom electrode (301) is preferred to be split into two halves, whereby the first halve performs function as a bottom electrode (301) and the second halve performs function as a top electrode despite not being positioned on top of the piezoelectric (302). The micromachined ultrasonic transducer propagates an ultrasonic wave when it is excited by appropriate electric fields by the electronic circuitry. To provide room for vibration of the micromachined ultrasonic transducer, a cavity (306) is formed below each micromachined ultrasonic transducer that extends from the passivation layer (103) to a portion of the inter-layer dielectric (102). The cavity (306) can be in vacuum condition.

Figure 2:
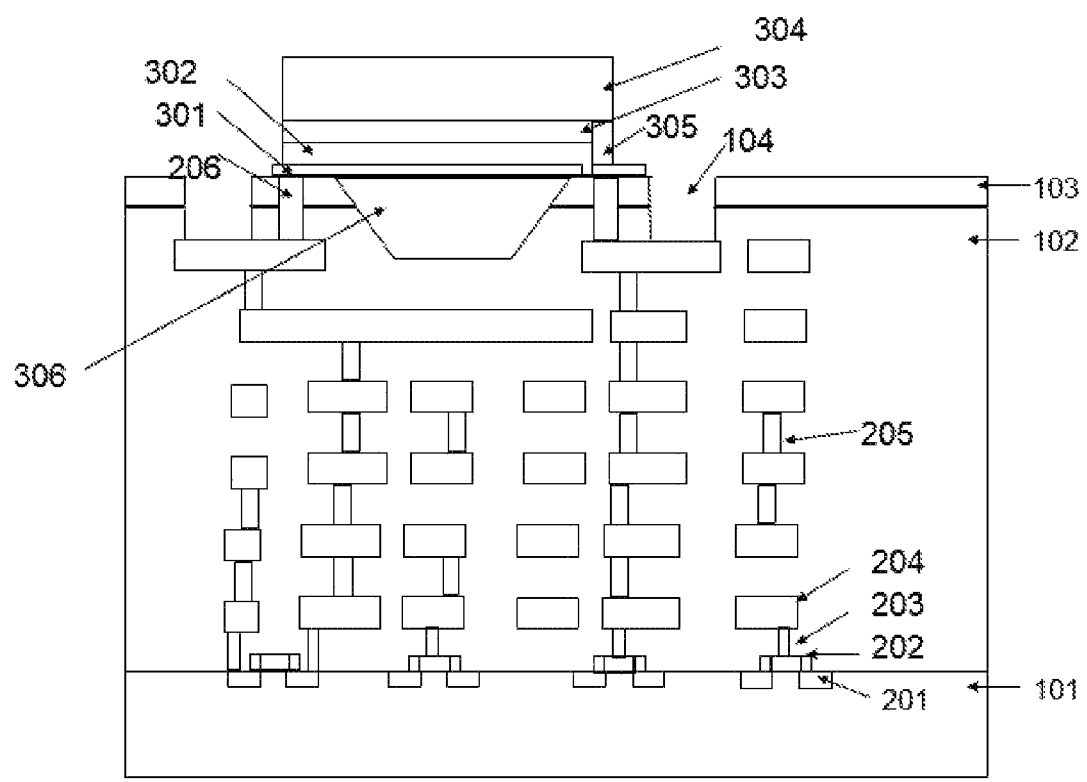
FIG. 2 shows a second preferred embodiment of a monolithic integrated device having a PMUT cell with a top electrode.

A second preferred embodiment of the invention is depicted in FIG. 2, wherein the monolithic integrated device comprises a substrate layer (101) that is the base of the device, an inter-layer dielectric (102) disposed in between the substrate layer (101) and below a passivation layer (103); and an electronic circuitry that comprises a plurality of metal layers (204) within the inter-layer dielectric (102) and supported by the substrate layer (101). The difference between the first preferred embodiment and the second preferred embodiment lies on the micromachine ultrasonic transducer, whereby the second preferred embodiment comprises a top electrode (303) on top of the piezoelectric (302) and below the elastic layer (304).

This invention further comprises an electrical connect (305) disposed below one or both ends of the elastic layer (304) that is connected to the electronic circuitry. The electrical connect serves to increase electrical integrity and allow electric connection between two adjacently positioned micromachined ultrasonic transducers. Preferably, the electrical connect (305) has a base portion for connecting to the bottom electrode (301) of an adjacent micromachined ultrasonic transducer. The electrical connect (305) can be part of the top electrode (303) such that the top electrode (303) can also serve as an electrical connect (305).

Components of the electronic circuitry include at least a source and drain component (201) in the substrate layer (101), at least a gate (202) in the inter-layer dielectric (102) that is connected to the source and drain component (201), a plurality of metal layers formed by one or more spaced apart metals (204), at least a contact component (203) for connecting the gate (201) to one of the metals (204), and vias (205) for connecting different metal layers. Electric field is imposed into the electronic circuitry for activating the micromachined ultrasonic transducer. A via contact (206) is used for contacting the bottom electrode (301) with the electronic circuitry for directing the electric field to the micromachined ultrasonic transducer.

The elastic layer (304) is a vibrating membrane that generates high pressure waves with the applied voltage signal. Materials applicable as the elastic layer (304) include but not limited to amorphous silicon, silicon dioxide, silicon nitride, silicon carbide, metallic nitride, bimetallic nitride, or metallic oxide. On the other hand, the piezoelectric (302) can be made of any one of these materials, which include aluminum nitride, aluminum scandium nitride, lead zirconate titanate or zinc oxide.

The passivation layer (103) functions as a protection layer for the electronic circuitry. In addition, the monolithic integrated device is formed with at least a bond-pad opening (104) that extends through the passivation layer (103) and partially into the inter-layer dielectric (102) until the bond-pad opening (104) reaches one of the metals (204) which is used as a bonding pad of the monolithic integrated device. These bond-pad openings (104) can be formed through etching to expose the bonding pad.

Figure 3:
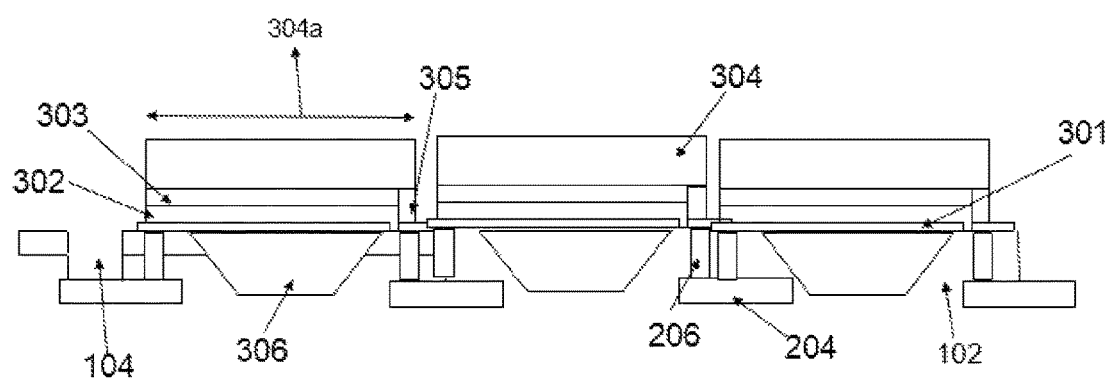
FIG. 3 shows the monolithic integrated device with multiple PMUT cells.

The monolithic integrated device described herein features the incorporation of micromachined ultrasonic transducer components within the CMOS substrate, whereby the cavity (306) is formed within the inter-layer dielectric (102) and the bottom electrode (301) and top electrode (303) of the micromachined ultrasonic transducer are connected directly to the CMOS substrate using the via contact (206) that connects to the electronic circuitry. A single CMOS substrate is only required for integrating with multiple PMUT cells. With reference to FIG. 3, multiple micromachined ultrasonic transducers are populated on the CMOS substrate with the cavity formed within the inter-layer dielectric (102). No separate bonding area is required for connecting the CMOS substrate with the micromachined ultrasonic transducer as bonding is not needed since this invention adapts the monolithic integration method. Further, the electrical connect (305) is in miniature size and its width can be less than 1 um such that the electrical connect (305) can be located within the effective PMUT area (304a) as indicated in FIG. 3.

What is claimed is:
1. A monolithic integrated device, comprising:
   a single substrate including:
      a substrate layer being a base of the device;
      an inter-layer dielectric disposed on top of the substrate layer and below a passivation layer; and
      an electronic circuitry formed within the inter-layer dielectric and supported by the substrate layer, the electronic circuitry comprises a plurality of spaced apart metal layers; and
   at least one micromachined ultrasonic transducer, each comprising:
      a bottom electrode disposed on top of the passivation layer;
      a piezoelectric disposed on top of the bottom electrode; and
      an elastic layer positioned on top of the piezoelectric;
      wherein the monolithic integrated device is formed with a cavity within the single substrate and below each micromachined ultrasonic transducer, the cavity extends from the passivation layer to a portion of the inter-layer dielectric;
      wherein the micromachined ultrasonic transducer connected to the electronic circuitry is built on the single substrate.

2. The monolithic integrated device according to claim 1, wherein the bottom electrode is split into two halves.

3. The monolithic integrated device according to claim 1, further comprising a top electrode in between the elastic layer and the piezoelectric.

4. The monolithic integrated device according to claim 1, further comprising an electrical connect disposed below one or both ends of the elastic layer and connected to the electronic circuitry.

5. The monolithic integrated device according to claim 4, wherein the electrical connect has a base portion for connecting to the bottom electrode of an adjacent micromachined ultrasonic transducer.

6. The monolithic integrated device according to claim 1, wherein the electronic circuitry includes at least a source and drain component in the substrate layer.

7. The monolithic integrated device according to claim 6, wherein the electronic circuitry includes at least a gate in the inter-layer dielectric, each connected to the source and drain component.

8. The monolithic integrated device according to claim 7, wherein the electronic circuitry includes at least a contact component for connecting any one or combination of the source and drain component and the gate to one of the metal layers.

9. The monolithic integrated device according to claim 1, wherein the electronic circuitry comprises one or more vias for connecting different metal layers.

10. The monolithic integrated device according to claim 1, wherein the electronic circuitry comprises at least one via contact for connecting the bottom electrode to the metal layer of the electronic circuitry.

11. The monolithic integrated device according to claim 1, wherein the monolithic integrated device is created with at least a bond-pad opening that extends through the passivation layer and partially into the inter-layer dielectric until the bond-pad opening reaches one of the metal layers.

12. The monolithic integrated device according to claim 1, wherein the electronic circuitry is a CMOS device.

13. The monolithic integrated device according to claim 1, wherein the elastic layer is any one of amorphous silicon, silicon dioxide, silicon nitride, silicon carbide, metallic nitride, bimetallic nitride, or metallic oxide.

14. The monolithic integrated device according to claim 1, wherein the piezoelectric is any one of aluminium nitride, aluminium scandium nitride, lead zirconate titanate or zinc oxide.

15. A monolithic integrated device, comprising:
   a single substrate including:
      a substrate layer being a base of the device;
      an inter-layer dielectric disposed on top of the substrate layer and below a passivation layer; and
      an electronic circuitry formed within the inter-layer dielectric and supported by the substrate layer, the electronic circuitry comprises a plurality of spaced apart metal layers; and
   at least one micromachined ultrasonic transducer, each comprising:
      a bottom electrode disposed on top of the passivation layer;
      a piezoelectric disposed on top of the bottom electrode;
      a top electrode disposed on top of the piezoelectric; and
      an elastic layer positioned on top of the top electrode;
      wherein the monolithic integrated device is formed with a cavity within the single substrate and below that each micromachined ultrasonic transducer, the cavity extends from the passivation layer to a portion of the inter-layer dielectric;

wherein the micromachined ultrasonic transducer connected to the electronic circuitry is built on the single substrate.

* * * * *